(12) United States Patent
Meyer et al.

(10) Patent No.: US 6,400,148 B1
(45) Date of Patent: Jun. 4, 2002

(54) USE OF REDUNDANT DATA FOR LOG QUALITY MEASUREMENTS

(75) Inventors: Wallace Harold Meyer, Spring; Songhua Chen, Katy, both of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/558,987

(22) Filed: Apr. 27, 2000

Related U.S. Application Data

(63) Continuation-in-part of application No. 09/483,336, filed on Jan. 14, 2000, which is a continuation-in-part of application No. 09/031,493, filed on Feb. 26, 1998, now Pat. No. 6,060,884, which is a continuation-in-part of application No. 08/675,178, filed on Jul. 3, 1996, which is a continuation of application No. 08/212,257, filed on Mar. 14, 1994, now abandoned.

(51) Int. Cl.[7] .................................................. G01V 3/00
(52) U.S. Cl. ....................................... 324/303; 324/300
(58) Field of Search ................................. 324/303, 307, 324/300, 309, 312, 322, 339; 702/7; 364/422

(56) References Cited

U.S. PATENT DOCUMENTS

| | | | |
|---|---|---|---|
| 4,471,436 A | 9/1984 | Schaefer et al. ............ 364/422 |
| 4,499,421 A | 2/1985 | Sinclair ....................... 324/339 |
| 5,023,551 A | 6/1991 | Kleinberg et al. .......... 324/303 |
| 5,452,761 A | 9/1995 | Beard et al. ................ 166/250 |
| 5,666,057 A | 9/1997 | Beard et al. ................ 324/339 |
| 5,781,436 A | 7/1998 | Forgang et al. ............ 364/422 |
| 5,889,729 A | 3/1999 | Frenkel et al. ................ 367/73 |
| 5,999,883 A | 12/1999 | Gupta et al. .................... 702/7 |

*Primary Examiner*—Edward Lefkowitz
*Assistant Examiner*—Brij B. Shrivastav
(74) *Attorney, Agent, or Firm*—Madan, Mossman & Sriram, P.C.

(57) ABSTRACT

In one embodiment of the invention, an induction logging system is used to measure selected formation and borehole parameters of interest and simultaneously provide indications of the quality of the selected measurements. One or more transmitter-receiver pairs are employed with the transmitter components operating at one or more frequencies. The induction logging system may be a conventional system with coil axes parallel to the borehole axis or may be a transverse induction logging system including coil axes inclined to the borehole axis. A model of the response characteristics of the borehole instrument is also employed. By using a subset of the measurements, the parameters of interest are determined and an expected value of the remaining measurements is made. A comparison of the actual and expected values of the remaining measurements serves as a quality control check on the equipment and on the accuracy of the model.

15 Claims, 3 Drawing Sheets

USE OF REDUNDANT DATA FOR LOG QUALITY MEASUREMENTS

REFERENCE TO RELATED APPLICATIONS

This application is a continuation-in-part of application Ser. No. 09/031,493 filed on Feb. 26, 1998, now U.S. Pat. No. 6,060,884, which is a continuation-in-part of application Ser. No. 08/675,178, filed on Jul. 3, 1996, which was a continuation of application Ser. No. 08/212,257 filed on Mar. 14, 1994, now abandoned. This application is also a continuation-in-part of application Ser. No. 09/483,336, filed on Jan. 14, 2000.

FIELD OF THE INVENTION

This invention is related to the determination of log quality using redundant measurements.

BACKGROUND OF THE INVENTION

This invention is directed toward quality control in the measurement of geophysical parameters of earth formations penetrated by a borehole. Co-pending U.S. patent application Ser. No. 08/675,178, filed on Jul. 3, 1996 discloses a method for quality control of propagation resistivity techniques using spaced transmitters operating at different frequencies and a plurality of longitudinally spaced receivers. An electromagnetic wave is propagated from the transmitting antenna coil into the formation in the vicinity of the borehole and is detected as it pass the receiving antennas. The basic or "raw" parameters measured by the receivers are the phase and the amplitude of the passing wave. The downhole instrument is conveyed along the borehole making a plurality of raw measurements as a function of depth within the borehole from which geophysical parameters of interest are computed as a function of depth within the borehole. It is quite common in the prior art to first combine raw data measurement and then to compute parameters of interest from these process measurements. A typical example is the computation of apparent resistivity from the difference in phase of signals detected at receivers at different longitudinal spacings from the transmitter. A second example is the computation of apparent resistivity from the ratio of the amplitude of signals detected at the longitudinally space receivers. Such preprocessing or data combination is performed primarily to eliminate the gross effects of the borehole and is well known in the prior art.

The '178 application is directed toward the simultaneous measurement of a plurality of parameters associated with the formation and borehole environment, and a quantitative measure of the quality of such raw measurements or uncertainty associated with such raw measurements. Parameters of interest selected may include the resistivity of the formation from which hydrocarbon saturation is computed, invasion profiles of the drilling fluid which are indicative of the permeability of the formation, and perhaps physical characteristic of the well bore itself such as diameter, ellipticity, and rugosity.

In the '178 application, non-linear inversion techniques are used to determine the set of selected unknown parameters which, through the model, predicts a tool response which most closely matches the thirty two measured raw data points. The predicted tool responses and the measured tool responses will exhibit no discrepancies only if (a) there is no error associated with the measured data and (b) if the model represents without error the response of the instrument in every encountered borehole and formation condition. This is because there are more measured data points than unknown variable parameters in the model. Any degree of non-conformance or "mismatch" of the model data and the measured data is a measure of inaccuracy of either the data or the model or both the data and the model. In all cases the determined non-conformance is treated as a quality indicator for the determined parameters of interest. In other words, an uncertainty is attached to each parameter selected by the analyst based upon the goodness of fit between the model and the measured data. Obtaining formation parameters from observations at multiple frequencies and/or multiple source-receiver offsets involves the solution of an overdetermined system of equations.

A similar situation arises in obtaining formation parameters in induction logging techniques. For example, U.S. Pat. No. 5,452,761 to Beard et al, having the same assignee as the present application and the contents of which are fully incorporated herein by reference, discloses an apparatus and method for digitally processing signals received by an induction logging tool having a transmitter and a plurality of receivers. An oscillating signal is provided to the transmitter, which causes eddy currents to flow in a surrounding formation. The magnitudes of the eddy currents are proportional to the conductivity of the formation. The eddy currents in turn induce voltages in the receivers. The received voltages are digitized at a sampling rate well above the maximum frequency of interest. The digitizing window is synchronized to a cycle of the oscillating current signal. Corresponding samples obtained in each cycle are cumulatively summed over a large number of such cycles. The summed samples form a stacked signal. Stacked signals generated for corresponding receiver coils are transmitted to a computer for spectral analysis. Transmitting the stacked signals and not all the individually sampled signals, reduces the amount of data that needs to be stored or transmitted. A Fourier analysis is performed on the stacked signals to derive the amplitudes of in-phase and quadrature components of the receiver voltages at the frequencies of interest. From the component amplitudes, the conductivity of the formation can be accurately derived. The Beard patent also teaches the use of analyzing data at multiple frequencies. These multiple frequencies may be obtained either by activating the transmitter at a plurality of frequencies, or, in a preferred embodiment, by a harmonic analysis of the data. As taught in the Beard patent, single frequency data modulated by a square pulse provides a signal that is rich in odd harmonics. Observations at multiple frequencies and solving for formation parameters gives an overdetermined system of equations, as in the '178 application.

U.S. Pat. No. 5,666,057 to Beard et al, the contents of which are fully incorporated herein by reference, teaches a multifrequency method of correcting for the so-called "skin-effect" and obtaining apparent conductivity of formations using induction logging tools. U.S. Pat. No. 5,889,729 to Frenkel et al having the same assignee as the present application, and the contents of which are fully incorporated herein by reference, discloses a method for 2-D inversion of induction logging data. Included therein is a step of 2-D forward modeling of induction logging data and the inversion of such data. U.S. Pat. No. 5,781,436 to Forgang et al, and U.S. Pat. No. 5,999,883 to Gupta et al., the contents of both of which are incorporated herein by reference, disclose the inversion of transverse induction logging data. A Transverse Induction Logging Tool (TILT) from which such data are obtained comprises a plurality of transmitters and receivers that have axes inclined to each other. Where the borehole axis is inclined to the bedding, such devices are able to determine apparent vertical and horizontal conductivities that are able to delineate resistive hydrocarbon bearing beds more accurately than conventional induction logging tools.

Solution of overdetermined systems of equations is also involved in Nuclear Magnetic Resonance (NMR) logging. This technique involves using NMR logging tools and methods for determining, among other things porosity, hydrocarbon saturation and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

U.S. Pat. No. 5,023,551 issued to Kleinberg discloses an NMR pulse sequence that has an NMR pulse sequence for use in the borehole environment which combines a modified inversion recovery (FIR) pulse sequence with a series of more than two, and typically hundreds, of CPMG pulses according to $$[W_i\text{-}180\text{-}TW_i\text{-}90\text{-}(t\text{-}180\text{-}t\text{-}echo)_j]_i$$

where j-1,2, ... J and J is the number of echoes collected in a single Carr-Purcell-Meiboom-Gill (CPMG) sequence, where i=1, ... I and I is the number of waiting times used in the pulse sequence, where $W_i$ are the recovery times, $TW_i$ are the wait times before a CPMG sequence, and where t is the spacing between the alternating 180° pulses and the echo signals. Although a conceptually valid approach for obtaining $T_1$ information, this method is extremely difficult to implement in wireline, MWD, LWD or MWT applications because of the long wait time that is required to acquire data with the different TWs.

Data may be acquired with different wait times and/or at different frequencies. In such cases, redundant measurements are made of basically the same physical parameters, viz., the distribution of $T_1$ and $T_2$ values of the formation. The data may be acquired in the same or different logging passes and it would be desirable to have a method for checking the consistency of the data, the validity of the model, and the reliability of the measurements.

The current invention provides means and methods for determining error which can be related to uncertainty associated with geophysical parameters measured with a downhole instrument of any of the types previously described. The user of the information, or "analyst", selects the parameters of interest which might include the resistivity (or conductivity) of the formation, the dielectric constant of the formation, the longitudinal and transverse relaxation times, or perhaps the degree to which drilling fluids invade the formation in the vicinity of the borehole. The analyst's primary interests are usually the determination of the hydrocarbon saturation, porosity and permeability of the formations penetrated by the borehole. It is highly desirable to make such measurements while drilling or soon after the drilling of the well borehole so that critical economic decisions concerning the amount and producibility of hydrocarbons in place can be made. Based upon this information, the well will either be completed or abandoned. The accuracy and precision of geophysical parameters selected to make such critical decisions is also of prime importance. The error measurements provided by the current invention can also be used to indicate equipment malfunctions of both the electrical and mechanical types. Although prior art teaches means and methods of measuring a wide range of geophysical parameters using electromagnetic techniques, little, if any, emphasis is placed upon determining the quality of the measurements. Usually the analyst can only rely on past experience in assigning, at best, qualitative estimates of the quality of the measurements obtained from the borehole instrument and associated system. Any error analysis is usually performed long after the measurements are made and usually not at the well site. Stated another way, prior art does not provide means and methods for determining the quality of electromagnetic based geophysical measurements in real-time, although real-time or near real-time economic and operational decisions are made based upon these measurements.

There is critical need for quantitative indications of the quality of geophysical measurements made in formations penetrated measurements simultaneous with the measurements made in formations penetrated by a borehole. More particularly there is a need for such quality measurements simultaneous with the measurements of parameters of interest. Knowledge of these parameters weighs so heavily in decision to complete or abandon the well. The present invention provides this very information by providing means and methods for measuring geophysical parameters selected by the analyst and simultaneously yielding quantitative measurements of the quality or error associated with the measurements of the selected parameters.

SUMMARY OF THE INVENTION

This invention is directed toward the redundant measurement of a plurality of parameters associated with the formation and borehole environment, and a quantitative measure of the quality of such raw measurements or uncertainty associated with such raw measurements. The measurements may be made simultaneously or in multiple passes. In the case of resistivity logging, parameters of interest selected may include the resistivity of the formation from which hydrocarbon saturation is computed, invasion profiles of the drilling fluid which are indicative of the permeability of the formation, and perhaps physical characteristic of the well bore itself such as diameter, ellipticity, and rugosity. The borehole related parameters might be used by the analyst to determine, as an example, the rock mechanics of the formation. In the case of NMR logging, one of the parameters of interest is the $T_1$ distribution time that characterizes the porosity of the formatin. As discussed previously, errors associated with the measurements are critical in the decision concerning-completion or abandonment of the well. Information concerning completion or abandonment of the well. Information concerning rock mechanics might guide the analyst in perforating after casing has been set or even in the design of hydraulic formation fracture operations subsequent to the setting of casing. The invention allows the analyst to choose parameters needed to make informed decisions as long as the total number of chosen parameters is less than the number of measurements made. Choices of parameters can vary from well to well depending upon need.

In one embodiment of the invention, measurements are made with an induction logging tool having a plurality of transmitters and receivers. In conventional logging tools, the transmitters and receiver coils are coaxial with the tool axis. In Transverse Induction Logging Tools (TILT), one or more of the transmitter and receiver coils are inclined to the axis of the tool so as to give measurements indicative of the horizontal and vertical conductivity of the formation. Two types of problems are addressed: one is the so-called "skin-effect" correction and the other is the inversion of the corrected data to give a layered model of resistivity of the formation. Both types of problems involve solution of an overdetermined set of equations.

In another embodiment, the method of the invention is used in the analysis of NMR data. Two possible applications are addressed. In one application, data acquired with multiple wait times are analyzed and compared for quality control. In another application, multifrequency NMR data are analyzed for consistency.

BRIEF DESCRIPTION OF DRAWINGS

So that the manner in which the above cited features, advantages and object of the present invention are obtained and can be understood in detail, more particular description of the invention, briefly summarized above, may be had by reference to the embodiments thereof which are illustrated in the appended drawings. It is to be noted, however, that the appended drawings illustrate only typical embodiments of the invention and are therefore not to be considered limiting of the scope for the invention may admit to other equally effective embodiments.

DETAILED DESCRIPTION OF THE PREFERRED EMBODIMENT

Figure 1:
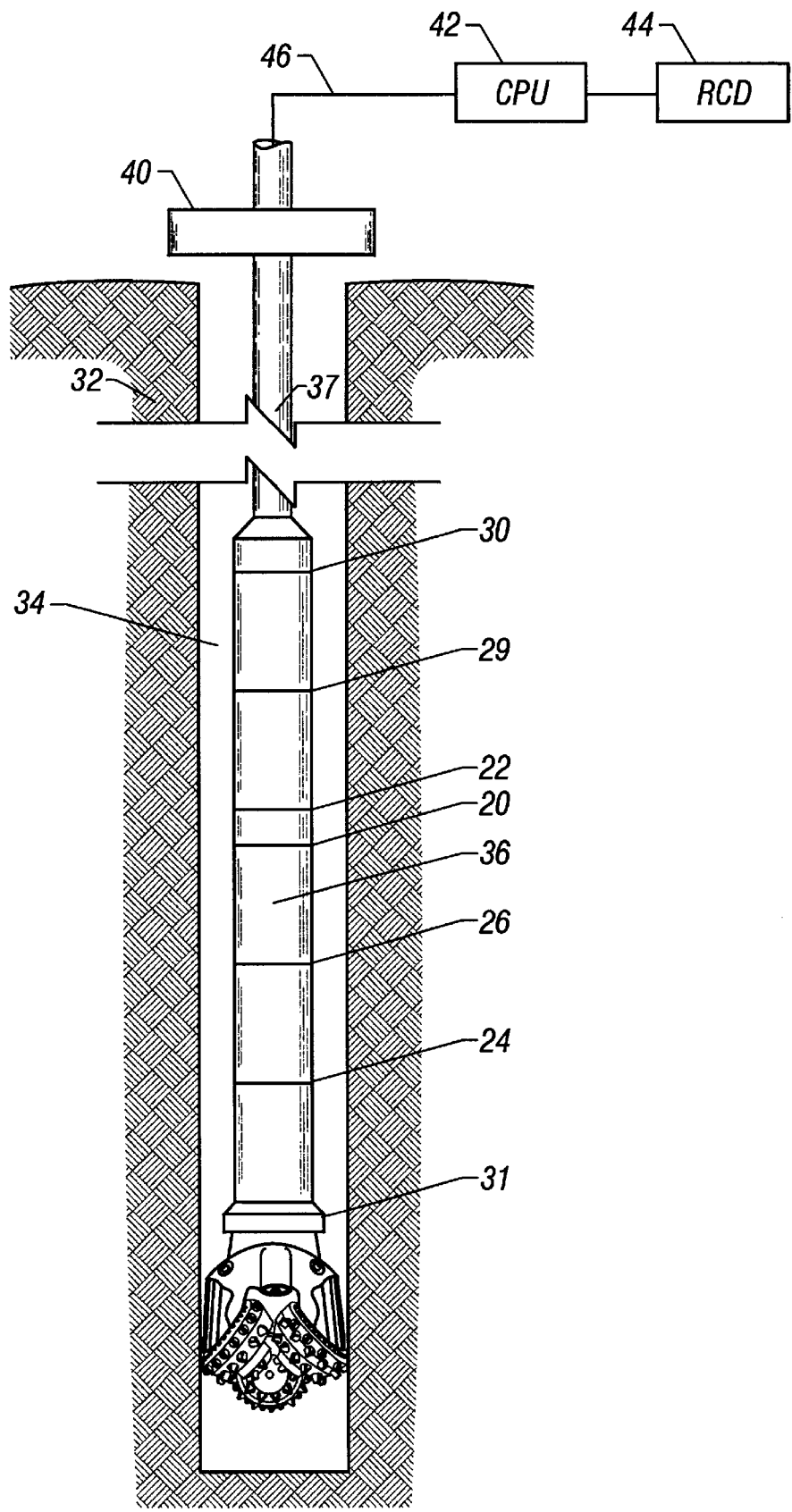
FIG. 1 illustrates the invention in a measurement while drilling (MWD) embodiment.

The invention maybe employed in a measurement while drilling (MWD) or wireline logging environment as discussed in co-pending United States Patent Application. One embodiment in an MWD environment is illustrative in a very general manner in FIG. 1. The drill bit 31 is attached to a metallic drill collar 36 which in turn is mounted on the wellbore drilling string 37. This assembly shown suspended in a wellbore 34 which penetrates the earth formation 32. A means for rotating the drill string 37 is identified by the numeral 40. Four transmitter coils of one or more turns are identified by the numerals 26, 24, 29 and 30. The axis of the coils are coincident with the axis of the drill collar 36. The coils are electrically insulated from and slightly recessed within the outer diameter of the drill collar, thereby comprising integral elements of the collar assembly. Two receiver coils are identified by the numerals 20 and 22. The geometries of these coils are quite similar to the geometries of the transmitter coils and again comprise integral elements of the collar assembly 36. Power sources control circuitry for the transmitter and receivers are internal to the drill collar 36 and are not shown. Data recorded by the receivers can either be transmitted in real-time to the surface using drilling fluid pulsing means (not shown) contained within the drill collar 36 for a later retrieval. For the real-time data transmission embodiment, signals from the receivers are transmitted to the surface by a path means generally denoted by the numeral 46, transferred to CPU unit 42 for processing and correlated with depths from the drill collar depth indicator (not shown), and output to recorder 44 which displays the computed parameters of interest as a function of depth at which the input measurements were made. An alternate embodiment comprises a processor unit (not shown) mounted within the drill collar 36 to perform data processing downhole. Memory capacity and telemetry channel bandwidth is usually limited in MWD borehole devices. In order to utilize the limited memory capacity and telemetry channel bandwidth most effectively, it is often more efficient to process raw data downhole and store processed results rather than the more voluminous raw data.

Figure 2:
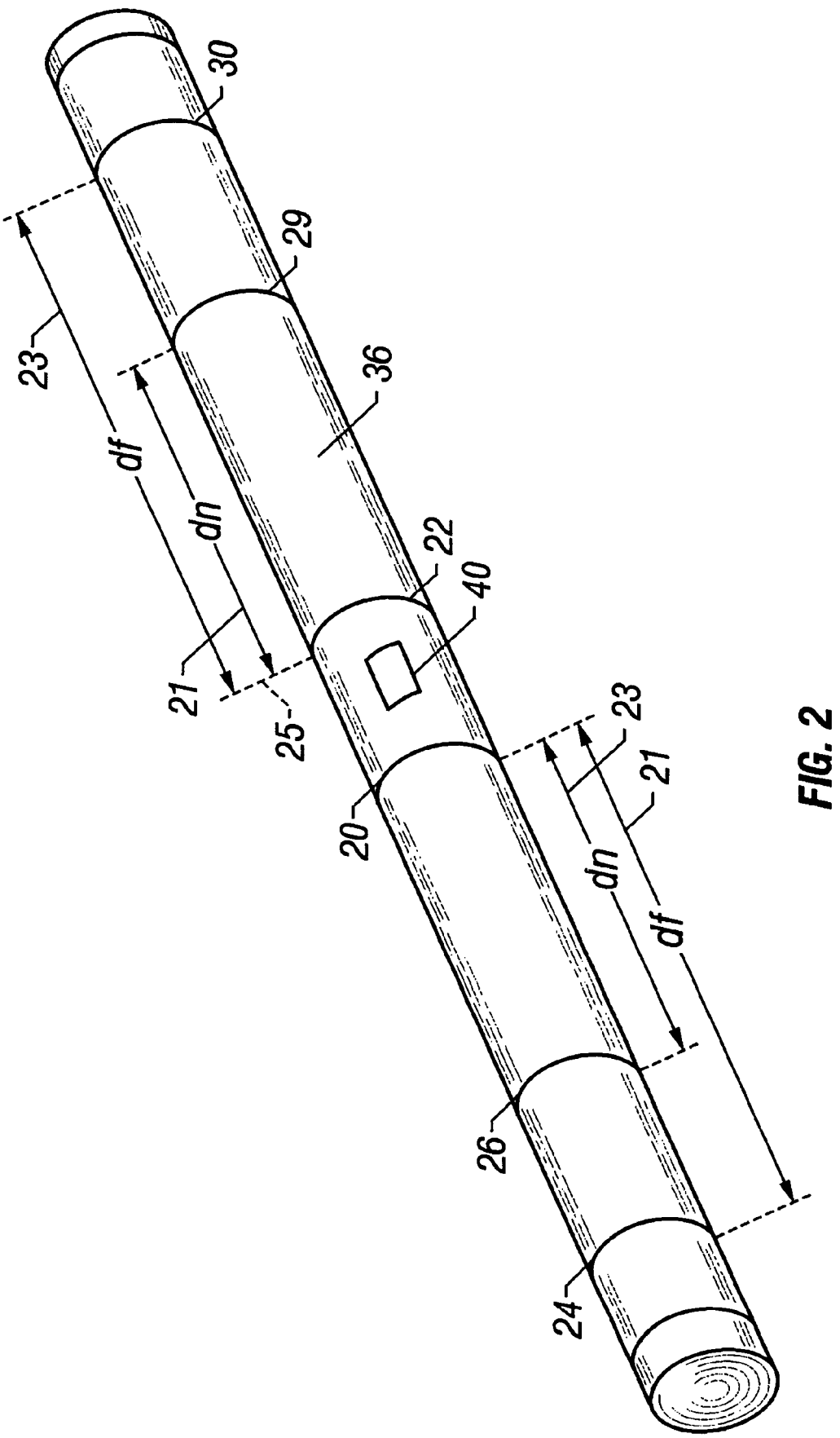
FIG. 2 illustrates in detail the drill collar comprising the transmitter and receiver coil arrays.

The drill collar comprising the transmitter receiver coil array is shown in greater detail in FIG. 2. The two receiver coils are denoted by the numerals 20 and 22. Transmitter coils 26 and 24 are longitudinally spaced distances 23 and 21, respectively, from the receiver 20. The transmitter coils 29 and 30 are likewise longitudinally spaced distances 21 and 23, respectively, from the transmitter 22. Again, power sources and control circuitry for the transmitters and receivers are contained within the drill collar and are not shown. The symmetrical spacing pattern of transmitters and receivers about a point 25 midway between receivers 20 and 22 is preferred but not a necessary condition for the embodiment of the invention.

Transmitters 24, 26, 29 and 30 are activated sequentially at a first frequency $\omega_1$. The phase and amplitude of the induced electromagnetic signal is measured at the receiver nearest to each activated transmitter thereby yielding four measurements of parameters will be identified as $A_i$ and $P_i$, respectively, where (i=1, . . . , 4). The procedure is repeated at a second frequency $\omega_2$ yielding an additional four measurements of amplitude and for measurements of phase, identified hereafter as $A_i$ and $P_i$, respectively, where (i=5, . . . ,8). The entire procedure is then repeated for the receiver farthest from each activated transmitter yielding values of $A_i$ and $P_i$ where (i=9, . . . ,16). In summary, a total count of thirty two parameters is measured by the borehole instrument. The above combined procedure of transmitting at frequencies $\omega_1$ and $\omega_2$, and recording received signals is repeated sequentially as the instrument is conveyed along the borehole.

Parameters of interest related to the formation, near borehole, and borehole are selected by the analyst. These parameters might include formation resistivity, formation dielectric constant, radius of invasion of the drilling fluid, resistivity of the drilling fluid and perhaps the diameter of the borehole. The selected number of parameters must be less than thirty two so that the system of equations described in the following sections is over determined thereby permitting uncertainty associated with the selected parameters to be determined. For purposes of illustration, it will be assumed that he analyst selects n parameters to be determined, where n is less than thirty two.

The processing of the data to obtain the parameters of interest and the determination of uncertainty associated with these parameters can best be described using matrix notation. The system is written as $$[T] \times [M] = [X] \tag{1}$$

where $$[T] = \begin{bmatrix} T_{1,1} & T_{1,2} & \cdots & T_{1,32} \\ T_{2,1} & T_{2,2} & \cdots & T_{2,32} \\ \vdots & \vdots & \ddots & \\ T_{m,1} & T_{m,2} & \cdots & T_{m,32} \end{bmatrix} \tag{2}$$

$$[M] = \begin{bmatrix} A_1 \\ \vdots \\ A_{16} \\ P_1 \\ \vdots \\ P_{16} \end{bmatrix} \quad (3)$$

and $$[X] = \begin{bmatrix} x_1 \\ \vdots \\ x_m \end{bmatrix} \quad (4)$$

The matrix [T] represents the theoretical response of the borehole instrument calculated using appropriate electromagnetic modeling techniques for a broad range of formation and borehole conditions, the matrix [M] represents the thirty two raw data points measured by the borehole instrument, and the matrix [X] represents the formation and borehole parameters selected by the analyst to be determined. Although the solution of the matrix equation (1) to attain the desired parameters represented by the vector [X] is viewed as linear, in this case the element of the matrix [T] can be dependent upon the elements of [X]. The solution of equation (1) will, therefore, require a non-linear regression solution such as a ridge regression.

Once equation (1) has been solved for [X], an inverse matrix operation is performed to generate a synthetic matrix of the measured quantities denoted as [M']. That is, $$[\hat{T}] \times [X] = [\hat{M}'] \quad (5)$$

where $$[\hat{T}] = \begin{bmatrix} \hat{T}_{1,1} & \hat{T}_{1,2} & \cdots & \hat{T}_{1,m} \\ \vdots & \vdots & \ddots & \vdots \\ \hat{T}_{32,1} & \hat{T}_{32,2} & \cdots & \hat{T}_{32,m} \end{bmatrix} \quad (6)$$

and $$[\hat{M}] = \begin{bmatrix} \hat{A}_1 \\ \vdots \\ \hat{A}_{16} \\ \hat{P}_1 \\ \vdots \\ \hat{P}_{16} \end{bmatrix} \quad (7)$$

The mismatch between the measured parameters, [M], and the predicted values of the measured parameters [$\hat{m}$] is a measure of quality of the parameters of interest, [X]. If $$[\hat{M}] \approx [M] \quad (8)$$

then there is little uncertainty associated with the computed values [X] indicating that the quality of the measured data [M] and the model representing the response of the instrument [T] are both good. If, however, $$[\hat{M}] \neq [M] \quad (9)$$

it can be concluded that either the measured data [M] are of poor quality or the model of the tool response represented [T] is inadequate or both conditions have occurred. It has been determined that in many cases, the model is quite reliable and error in the model is only a minor contributor to the observed error. It follows, therefore that for these cases the observed error is usually attributable to equipment malfunctions. The degree of mismatch of [M'] and [M] is indicative of the magnitude of the uncertainty or error in the computed parameters of interest, [X]. Non-linear regression techniques suitable for application in this invention are described in the publication "Inversion of 2 MHZ Propagation Resistivity Logs" by W. H. Meyer, SPWLA 22nd Annual Logging Symposium, June 14–17, 1992, Paper H.

One of the novel features of the present invention is based upon the great deal of redundancy in the measurements. Based on this redundancy, it is possible to make checks of the quality of the measurements and identify possible problems with particular combinations of sources and receivers. This is illustrated by the following example.

The starting point is, as before, equation (1). However, instead of using all the measurements, 32 in the case of equations (2) and (3), only a subset of the measurements are used. For example, only measurements 1–16 are used. In this case, the matrices [T] and [M] are given by:

$$[T] = \begin{bmatrix} T_{1,1} & T_{1,2} & \cdots & T_{1,16} \\ \vdots & \vdots & \ddots & \vdots \\ T_{m,1} & T_{m,2} & \cdots & T_{m,16} \end{bmatrix} \quad (10)$$

and $$[M] = \begin{bmatrix} A_1 \\ \vdots \\ A_8 \\ P_1 \\ \vdots \\ P_8 \end{bmatrix} \quad (11)$$

After solving equations 1, 10 and 11 for [X], the inverse matrix operation is performed according to equation (5) to get $$[\hat{M}] = \begin{bmatrix} \hat{A}_9 \\ \vdots \\ \hat{A}_{16} \\ \hat{P}_9 \\ \vdots \\ \hat{P}_{16} \end{bmatrix} \quad (12)$$

where $$[\hat{T}] = \begin{bmatrix} \hat{T}_{17,1} & \hat{T}_{17,2} & \cdots & \hat{T}_{17,m} \\ \vdots & \vdots & \ddots & \vdots \\ \hat{T}_{32,1} & \hat{T}_{32,1} & \cdots & \hat{T}_{32,m} \end{bmatrix} \quad (13)$$

By these operations, eight measurements of amplitude and phase are used to predict a value of the remaining eight measurements. A comparison between the actual and predicted value of the remaining eight measurements is a useful diagnostic. If the difference is small, then it indicates that the overall quality of the data measurements is satisfactory. If, however, the actual and predicted value of the remaining eight measurements is large, then there is something systematically wrong, either with some of the measurements or with the theoretical response of the borehole using electromagnetic modeling techniques. The subset of measurements used in derivation of the parameters of interest can correspond to a subset of the frequencies, a subset of the transmitters, a subset of the receivers, a subset of transmitter-receiver distances or any other subset. If a subset of transmitter-receiver distances is used to predict measurements of another subset of transmitter receiver distances and the errors are large, a likely cause of error lies in the modeling technique used in the theoretical response of the borehole. For example, if the borehole shape is elliptical whereas the model is based upon a circular borehole shape, a systematic error will result if data from one transmitter-receiver distance is used to predict measurements at another transmitter-receiver distance. Similarly, other environmental causes, such as changes in thickness of a mudcake inside the borehole will also lead to systematic errors as a function of transmitter-receiver distance.

If, however, no systematic error with transmitter-receiver distance is found, the modeling technique is reliable and the problem must lie elsewhere. By experimentation with various subsets, the source of an error can be identified with a particular transmitter, a particular receiver or a particular frequency oscillator.

Figure 3:
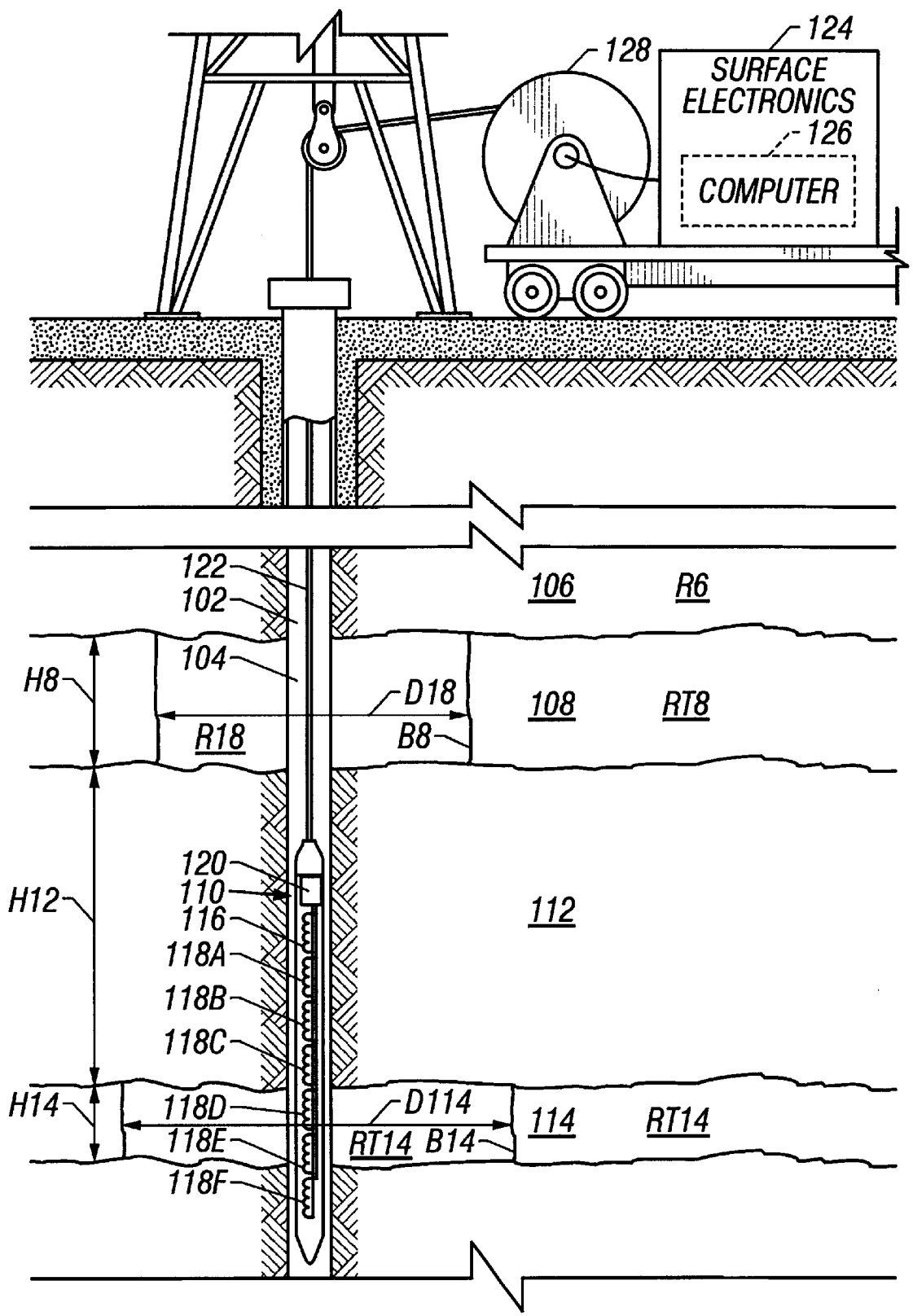
FIG. 3 illustrates a drilling system including the present invention.

U.S. Pat. No. 5,666,057 to Beard et al, the contents of which are fully incorporated herein by reference, teaches a multifrequency method of correcting for the so-called "skin-effect" and obtaining apparent conductivity of formations using induction logging tools. Referring now to FIG. 3, and example of a prior art induction logging system is shown. Shown is an induction well logging instrument 110 disposed in a wellbore 102 penetrating earth formations. The earth formations are shown generally at 106, 108, 112 and 114. The instrument 110 is typically lowered into the wellbore 102 at one end of an armored electrical cable 122, by means of a winch 128 or similar device known in the art. The instrument described is meant only to serve as an example of, and is not meant to be an exclusive representation of induction well logging instruments which can generate signals usable for performing the process of the present invention. The instrument is therefore not to be construed as a limitation on the present invention.

The instrument 110 can include a telemetry/signal processing unit 120 (SPU). The SPU 120 can include a source of alternating current (not shown separately). The alternating current is generally conducted through a transmitter coil 116 disposed on the instrument 110. Receiver coils 118A–118F can be disposed at axially spaced apart locations along the instrument 110. The SPU 120 can include receiver circuits (not shown separately) connected to the receiver coils 118A–118F for detecting voltages induced in each of the receiver coils 118A–118F. The SPU 120 can also impart signals to the cable 122 corresponding to the magnitude of the voltages induced in each of the receiver coils 118A–118F. It is to be understood that the number of transmitter and receiver coils, and the relative geometry of the transmitter and receiver coils shown in the instrument in FIG. 3 is not meant to be a limitation on the present invention. It is to be further understood that the receiver coils shown in FIG. 3 can either be single coils or a type of receiver coil known in the art as "mutually balanced" wherein each receiver coil includes a primary coil (not shown separately) and a second coil (not shown separately) wound in series connection and in inverse polarity to the primary coil (not shown separately) so as to reduce the effect of direct induction from the transmitter coil 116.

As is understood by those skilled in the art, the alternating current passing through the transmitter coil 116 induces eddy currents in the earth formations 106, 108, 112, 114. The eddy currents correspond in magnitude both to the electrical conductivity of the earth formations 106, 108, 112, 114 and to the relative position of the particular earth formation with respect to the transmitter coil 116. The eddy currents in turn induce voltages in the receiver coils 118A–118F, the magnitude of which depends on both the eddy current magnitude and the relative position of the earth formation with respect to the individual receiver coil 118A–118F.

The voltages induced in each receiver coil 18A–18F correspond to apparent electrical conductivity of all of the media surrounding the instrument 110. The media include the earth formations 106, 108, 112 and 114 and the drilling mud 104 in the wellbore 102. The degree of correspondence between the voltages induced in a particular receiver coil, and the electrical conductivity of the particular earth formation axially disposed between the particular receiver coil and the transmitter coil 116, can depend on the vertical thickness of the particular earth formation, such as shown at H8 for earth formation 108. A more closely spaced receiver coil such as 118A would have more of its voltage induced by eddy currents flowing from entirely within a thinner formation such as 114 (having a thickness shown at H14), than would be the case for a longer spaced receiver coil such as 118F. Conversely, the eddy currents which induce the voltages in receiver coil 118A would more likely correspond to the conductivity within a zone such as shown at RI14, which is affected by fluid "invasion" into its pore spaces from the liquid phase of a fluid 104 used to drill the wellbore (commonly known as "drilling mud", the liquid phase known as "mud filtrate"). The radial distance from the center of the wellbore 102 to which the mud filtrate penetrates the particular earth formation can be different for each formation. A more deeply invaded zone DI14 in formation 114 is shown in comparison to a more shallow invaded zone DI8 in formation 108. Other formations, such as 106 and 112, may be substantially impermeable to fluid flow and therefore may not have invaded zones at all. The radial depth of invasion, such as DI8 or DI14, is typically not known at the time the instrument 110 is moved through the wellbore 102.

The drilling mud 104 itself can be electrically conductive. Eddy currents can flow in such conductive drilling mud, and therefore the voltages induced in each of the receiver coils 18A–18F can also partially depend on the conductivity of the mud 4 and the diameter of the wellbore, shown at D. As is understood by those skilled in the art, the wellbore diameter D is subject to variation as a result of "caving" or "washout". Devices (calipers) for measuring the wellbore diameter D are well known in the art, but are typically impractical to use in the process of correcting the receiver coil signals for the effects of eddy current flow in the wellbore 102.

The signals corresponding to the voltages in each receiver coil 18A–18F can be transmitted along the cable 122 to surface electronics 124. The surface electronics 124 can include detectors (not shown) for interpreting the signals from the instrument 110 and a computer 126 to perform the process according to the present invention on the signals transmitted thereto. It is to be understood that the SPU 120 could also be programmed to perform the process of the present invention. Processing the receiver coil signals in the computer 126 is a matter of convenience for the system designer and is not to be construed as a limitation on the present invention.

The correspondence between the magnitude of the voltages induced in each receiver coil 118A–118F and the conductivity of the media surrounding the instrument 110 is affected by a phenomenon referred to as the "skin effect". The voltage signals induced in each receiver coil 118A–118F can be used to determine the magnitude of the skin effect, so that a more precise value of the conductivity of the media surrounding the instrument 110 can be determined.

A particular advantage of using an apparatus like the one disclosed in the Beard et al '057 patent is that the transmitter coil described in the apparatus of the Beard et al '057 patent can be energized with alternating current having a plurality of different component frequencies, and the SPU as disclosed in Beard et al '057 is adapted to generate signals which can be interpreted as to the magnitude of the induced voltages at each one of the plurality of different component frequencies.

As described in the Beard '057 patent, measurements are made at a plurality of frequencies, for example, 10, 30, 50, 70, 90, 110, 130 and 150 kilohertz (KHz). These measurements may be made either by exciting the transmitter at these selected frequencies or by exciting the transmitter with a square wave of 110 kHz frequency and analysing the odd harmonics of the induced signal.

As disclosed in the Beard '057 patent, the apparent conductivity $\sigma_a$ as measured by the various coils of the induction logging tool may be expressed as a function of the frequency f by a polynomial relationship of the form $$\sigma_a = y_0 + y_1 f + y_2 f^2 + \ldots y_{n-1} f^{n-1} \quad (14)$$

where the $y_i$s represent polynomial coefficients of the polynomial expression that is to be solved, and n represents the number of unknowns, typically less than or equal to the number of frequencies m being analyzed.

A system of equations can be designed to solve the polynomial coefficients $$AY = \sigma_a \quad (15)$$

A can be represented as the matrix $$[A] = \begin{bmatrix} 1 & f_1 & f_1^2 & \cdots & f_1^{n-1} \\ 1 & f_2 & f_2^2 & \cdots & f_2^{n-1} \\ \vdots & \vdots & \vdots & \ddots & \vdots \\ 1 & f_m & f_m^2 & \cdots & f_m^{n-1} \end{bmatrix} \quad (16)$$

where the coefficients to be solved are expressed in the vector Y $$Y = (y_0, y_1, y_2, \ldots y_{n-1})^T \quad (17)$$

and the apparent conductivity values at each component frequency are expressed in the vector $$\sigma_a = (\sigma_1, \sigma_2, \sigma_3, \ldots \sigma_m)^T \quad (18)$$

The methodology described above with respect to the propagation resistivity logging tool may be used with respect to the solution of eqs. (15)–(18). Measurements may be made of the apparent conductivity at a number of frequencies and a subset of the measurements used to derive a polynomial fit. Using this derived polynomial fit, a prediction may be made about the apparent conductivity value at a frequency that is not used in the derivation of the polynomial. If the predicted and actual values of the apparent conductivity do not agree, then it is an indication that at that particular frequency, the measurements are suspect, possibly because of a resonance in the tool.

Once an apparent conductivity profile has been obtained, there are numerous methods in prior art for applying the so-called "shoulder effect" correction and deconvolving the apparent conductivity profile for the tool response function. See, for example, U.S. Pat. No. 4,471,436 to Schaefer et al. As would be known to those versed in the art, this is not a linear process. In the context of the present invention, the measurements made with an induction logging tool have a great deal of redundancy, and any subset of the measurements (common transmitter, common receiver, common transmitter-receiver, selected subset of frequencies) may be used to apply the skin effect correction and then derive a resisitivity model. This derived resistivity model may then be used to predict the value of measurements that would be made in other subsets of the measurements. Any discrepancy between the predicted and actual values of the other measurements may be used for quality control of the data.

U.S. Pat. Nos. 5,781,436 and 5,999,883 to Forgang et al and Gupta et al respectively, having the same assignee as the present application and the contents of which are fully incorporated herein by reference, teach methods for obtaining the horizontal and vertical conductivity of a transversely isotropic earth formation using a Transverse Induction Logging Tool (TILT). The device includes a plurality of transmitters and receiver coils with some of the coils inclined to the axis of the borehole. These measurements may be inverted to give a physical model of earth resisitivity that includes layer thicknesses, horizontal and vertical resistivities and an inclination angle of the tool to the layers. Using the methodology described above, this derived physical model may be used to predict measurements made by others of the plurality of transmitters and receivers for quality control.

The use of the method of the present invention is not limited to resistivity measurements. Co-pending U.S. patent application Ser. No. 09/483,336 having common inventorship with the present application and the contents of which are fully incorporated by reference, discloses a method for processing of Nuclear Magnetic Resonance (NMR) measurements acquired using multiple wait times.

NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

A typical NMR tool generates a static magnetic field $B_0$ in the vicinity of the wellbore, and an oscillating field $B_1$ in a direction perpendicular to $B_0$. This oscillating field is usually applied in the form of short duration pulses. The purpose of the $B_0$ field is to polarize the magnetic moments of nuclei parallel to the static field and the purpose of the $B_1$ field is to rotate the magnetic moments by an angle $\theta$ controlled by the width $t_p$ and the amplitude $B_1$ of the oscillating pulse. With the variation of the number of pulses, pulse amplitude, and pulse intervals, various pulse sequences can be designed to manipulate the magnetic moment, so that different aspects of the NMR properties can be obtained. For NMR logging, the most common sequence is the Carr-Purcell-Meiboom-Gill ("CPMG") sequence that can be expressed as TW-90-(t-180-t-echo)$_n$ After being tipped by 90°, the magnetic moment precesses around the static field at a particular frequency known as the Larmor frequency $\omega_0$, given by $\omega_0 = \gamma B_0$, where $B_0$ is the field strength of the static magnetic field and $\gamma$ is the gyromagnetic ratio. At the same time, the magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This gives a sequence of n echo signals.

The copending '336 application teaches the acquisition of NMR data with at least two different wait times TWS and TWL wherein TWS is shorter than TWL. TWS is long enough to fully polarize any water in the formation but only partially polarize any light hydrocarbons in the formation.

The pulse echo measurements made using the multiple wait times define an overdetermined system for the distribution of $T_1$ and $T_2$ of the formation. In the present invention, the data obtained using the short wait time TWS are used to obtain the distribution of $T_2$ for the formation. Next, using the assumption that $T_1 = k\, T_2$, where k is taken to be 1.5, the distribution of $T_1$ and $T_2$ is used to predict data that would be acquired with a longer wait time TWL. A comparison of the actual measurements with the predicted measurements serves as a check on the quality of the NMR data.

A similar method can be used wherein instead of, or in addition to, dual wait times for the acquisition of NMR data, the data are acquired at multiple frequencies of the RF pulses. Such a method may be used when the static magnetic field, as is commonly the case, has a significant field gradient, so that different frequencies of the RF pulse correspond to different portions of the formation being examined. U.S. Pat. No. 6,049,205 to Taicher et al, the contents of which are fully incorporated herein by reference, discloses the use of multiple CPMG sequences at different RF pulse frequencies to determine NMR properties of subsurface formations.

The above description may make other alternate embodiments of the invention apparent to those skilled in the art. It is, therefore, the aim of the appended claims to cover all such changes and modification as fall within the true spirit and scope of the invention.

What is claimed is:

1. A method for determining parameters of interest relating to earth formations penetrated by a borehole and error associated therewith, comprising:
   (a) providing a borehole instrument comprising a plurality of transmitter-receiver pairs, each said transmitter-receiver pair having a transmitter and receiver associated therewith;
   (b) operating each transmitter of said transmitter-receiver pairs at at least one operating frequency, thereby inducing eddy currents within the formation and the borehole, said eddy currents dependent on the parameters of interest of the formation;
   (c) measuring voltages in the plurality of receivers responsive to the induced eddy currents thereby obtaining a set of measurements indicative of the parameter of interest;
   (d) providing a model which relates said set of measurement to the parameters of interest by a set of equations, said equations comprising an overdetermined set;
   (e) selecting the parameters of interest which are to be determined;
   (f) obtaining an estimate of said selected parameters of interest by combining the model with a first subset of measurements selected from the set of measurements wherein the number of the selected parameters of interest is less than or equal to the number of measurements in the first subset of measurements; and
   (g) determining an error associated with said selected parameters of interest by utilizing the estimate of the selected parameters of interest and a second subset of measurements selected from the set of measurements.

2. The method of claim 1, wherein the at least one frequency of operation of the transmitter comprises a plurality of frequencies.

3. The method of claim 1, wherein measuring said voltages in the plurality of receivers further comprises measuring voltages corresponding to a plurality of harmonics of the at least one frequency.

4. The method of claim 2 wherein the first subset of measurements comprises all the measurements from the set of measurements having one of: (i) a selected transmitter, (ii) a selected receiver, (iii) a selected transmitter-receiver spacing, and (iv) a selected frequency.

5. The method of claim 3 wherein the first subset of measurements comprises all the measurements from the set of measurements having one of: (i) a selected transmitter, (ii) a selected receiver, (iii) a selected transmitter-receiver spacing, and (iv) a selected frequency.

6. The method of claim 1 wherein said model comprises at least one of (i) a model of the skin effect associated with the proximity of the borehole, and, (ii) a layered resisitivity model of the formation.

7. The method of claim 1 wherein said plurality of transmitter-receiver pairs further comprises at least one coil having an axis parallel to an axis of the borehole and at least one coil having an axis inclined to the axis of the borehole.

8. The method of claim 1 wherein said model comprises an inclination of an axis of the borehole to a bedding plane of the formation.

9. The method of claim 1 wherein determining said error further comprises:
   (i) using said model and said estimate of the selected parameters of interest for predicting values of the second subset of measurements, and
   (ii) comparing said predicted values of the second subset of measurements with measured values of the second subset of measurements.

10. The method of claim 1 wherein at least one of said plurality of transmitter-receiver pairs further comprises a transmitter having a coil with an axis orthogonal to a coil of the associated receiver.

11. The method of claim 1 wherein said model includes a zone of the formation invaded by drilling fluid.

12. The method of claim 1 wherein said model comprises a polynomial relationship between an apparent formation conductivity and frequency.

13. The method of claim 1 wherein said model comprises at least one of (i) a layer thickness, (ii) a vertical conductivity of a layer, (iii) a horizontal conductivity of a layer, and (iv) an inclination of an axis of the borehole instrument to a layer.

14. A method of determining a parameter of interest of a volume of earth formation in a reservoir adjacent a borehole, the method comprising:
   (a) using a magnet assembly on a borehole tool conveyed in the borehole at at least one depth for producing a static magnetic field in said volume of the formation thereby aligning nuclear spins within said volume parallel to a direction of the static field;
   b) producing a radio frequency (RF) magnetic field in said volume of the formation with an antenna on the borehole tool, said RF magnetic field having a direction orthogonal to a direction of the static field, the RF field including a first pulse sequence $TW_A$-90-(t-X-t-echo)$_j$ to produce a first echo train and at least one second pulse sequence $TW_B$-90-(t-X-t-echo)$_j$ to produce at least a second echo train, wherein 90 is a tipping pulse for tipping the nuclear spins at an angle substantially equal to ninety degrees to cause precession thereof, $TW_A$ is a first wait time, $TW_B$ is a second wait time, X is a refocusing pulse, and j=1, 2, ... J, where J is the number of echoes collected in a single sequence of pulses;

c) measuring with the borehole tool the first and at least one second echo train;

(d) obtaining an estimate of the parameter of interest from the first echo train;

(e) using the estimated value of the parameter of interest to obtain an estimated second echo train; and (f) obtaining a measure of reliability of the estimate of the parameter of interest by comparing said second echo train with the estimated second echo train.

15. A method of determining a parameter of interest of a volume of earth formation in a reservoir adjacent a borehole, the method comprising:

(a) using a magnet assembly on a borehole tool conveyed in the borehole at at least one depth for producing a static magnetic field in said volume of the formation thereby aligning nuclear spins within said volume parallel to a direction of the static field;

(b) producing a first radio frequency (RF) magnetic field in said volume of the formation with an antenna on the borehole tool, said RF magnetic field having a first frequency and a direction orthogonal to a direction of the static field, the first RF field including a first pulse sequence TW-90-(t-X-t-echo)$_j$ to produce a first echo train wherein 90 is a tipping pulse for tipping the nuclear spins at an angle substantially equal to ninety degrees to cause precession thereof, TW is a wait time, X is a refocusing pulse, and j=1, 2, ... $J_1$, where $J_1$ is the number of echoes collected in a single sequence of pulses;

(c) producing a second RF magnetic field in said volume of the formation with said antenna, said second RF magnetic field having a second frequency and a direction orthogonal to a direction of the static field, the second RF field including a second pulse sequence $TW_A$-90-(t-X-t-echo)$_j$ to produce a second echo train wherein 90 is a tipping pulse for tipping the nuclear spins at an angle substantially equal to ninety degrees to cause precession thereof, $TW_A$ is a second wait time, X is a refocusing pulse, and j=1, 2, ... $J_2$, where $J_2$ is the number of echoes collected in a single sequence of pulses;

(d) measuring with the borehole tool the first and at least one second echo train;

(e) obtaining an estimate of the parameter of interest from the first echo train;

(f) using the estimated value of the parameter of interest to obtain an estimated second echo train; and (g) obtaining a measure of reliability of the estimate of the parameter of interest by comparing said second echo train with the estimated second echo train.

* * * * *